United States Patent [19]

Werner

[11] Patent Number: 5,411,103

[45] Date of Patent: May 2, 1995

[54] MOISTURE AND SOIL CONSISTENCY PROBE

[75] Inventor: Mary K. Werner, Dayton, Ohio

[73] Assignee: M. W. Enterprises, Inc., Dayton, Ohio

[21] Appl. No.: 206,667

[22] Filed: Mar. 7, 1994

[51] Int. Cl.6 .............................................. G01N 1/04
[52] U.S. Cl. .................................... 175/20; 73/864.41
[58] Field of Search ................. 175/20, 58; 73/864.41, 73/864.43, 864.44, 869.45, 864.51, 864.61; 52/155; 135/118; 83/919; 411/451, 452, 456

[56] References Cited

U.S. PATENT DOCUMENTS

| 230,121 | 7/1980 | Frost | 73/864.64 X |
|---|---|---|---|
| 1,774,846 | 9/1930 | Rosenberg | 411/451 |
| 3,091,969 | 6/1963 | Romanchuck et al. | 73/863.31 |
| 3,373,464 | 3/1968 | Ansnit | 135/118 X |
| 3,618,447 | 11/1971 | Goins | 411/451 X |
| 3,738,176 | 6/1973 | Kerfoot | 73/425.4 R |
| 4,442,721 | 4/1984 | Singer | 73/863.31 |
| 5,121,643 | 6/1992 | Voloudakis | 73/864.41 |

OTHER PUBLICATIONS

Ad for Probe Rite, *Interiorscape*, Jan./Feb. 1994.

*Primary Examiner*—William P. Neuder
*Attorney, Agent, or Firm*—Gottman, Hagan & Schaeff Killworth

[57] ABSTRACT

A soil sampling probe includes a handle for grasping the probe and a rod member extending therefrom. The handle comprises an annular ring integrally formed with the rod member. A number of soil sampling slots are formed along in the rod member for collecting and retaining soil samples. The soil sampling slots slope inwardly and downwardly in the rod member. A substantially vertical rib is formed adjacent the slots to reinforce the rod member adjacent the soil sampling slots.

15 Claims, 2 Drawing Sheets

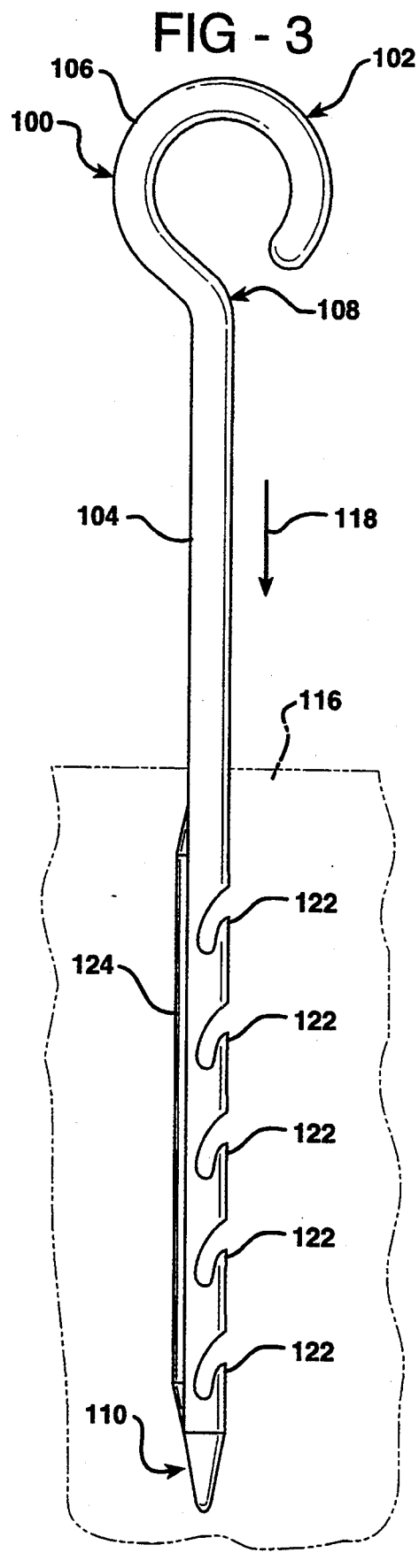
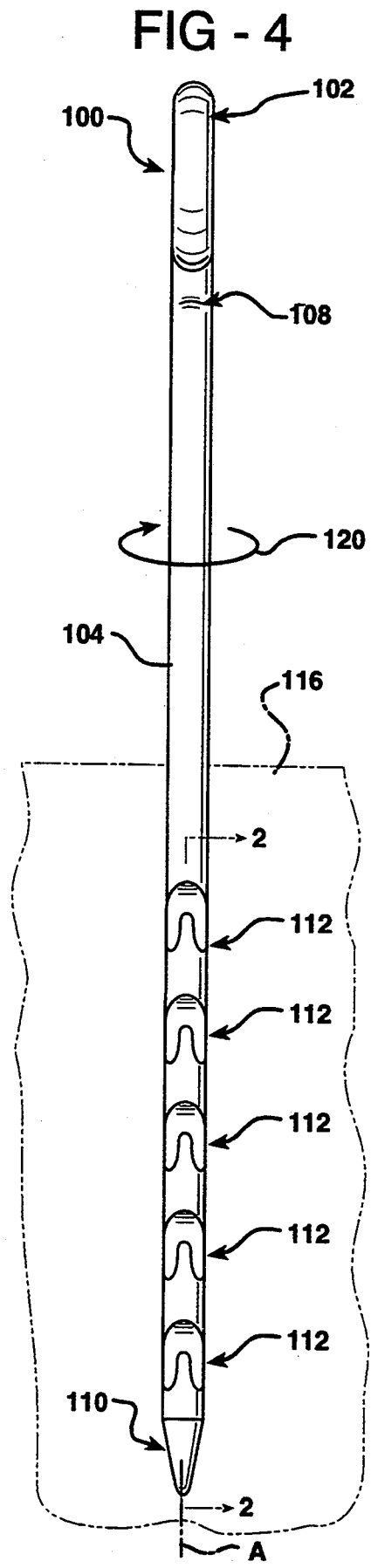

MOISTURE AND SOIL CONSISTENCY PROBE

BACKGROUND OF THE INVENTION

The present invention relates generally to soil sampling devices and, more particularly, to an easy to use, relatively inexpensive, structurally rigid, hand held soil sampling probe for substantially simultaneously obtaining soil samples at one or more soil depths to obtain information relative to the moisture content and consistency of the soil.

Numerous conditions determine the growth and overall health of a plant. For instance, the composition and moisture content of the soil must be carefully monitored and controlled to assure maximum plant health. Horiculturalists and gardeners monitor soil moisture and composition by continually collecting soil samples near the plant root base. The soil samples should be from a multiplicity of depths since both the moisture level and the elemental composition of the soil varies with depth. Further, the soil samples should be procured from the multiplicity of depths at substantially the same time to accurately monitor the soil.

Soil sampling tools are known in the art wherein soil samples are collected and retained in compartments, or pockets, formed in a cylindrical rod. One such soil sampling tool is disclosed in U.S. Pat. No. 5,121,643, issued to Voloudakis. The Voloudakis tool comprises a cylindrical rod having an insertable end for insertion into soil and a handle positioned opposite thereto. A plurality of collecting pockets are serially formed along the length of the rod for obtaining soil samples. Each collecting pocket has an arcuate vertical cross section with an opening on one side and defines an arc of greater than 180° such that lips are formed on each side of the opening to assist in collecting and retaining a soil sample.

Since the collecting pockets of the Voloudakis tool are substantially circular, the area of any one of the pockets is limited for any particular rod. If any of the pockets are too large, the effective cross sectional area of the rod at that pocket may be insufficient for the rod to retain its rigidity when inserted into soil. To increase the pocket size in the Voloudakis tool, the diameter of the rod may be increased. However, any increase in the diameter of the rod concomitantly increases the insertion force required to use the tool, increases the manufacturing cost of the tool, and increases the likelihood that the tool will contact plant roots.

Alternatively, the tool may be fabricated from a more rigid material. The commercial embodiment of the Voloudakis tool is, in fact, constructed of cold-rolled steel. Unfortunately, increasing the strength of the material may increase the weight of the tool or increase the manufacturing cost of the tool. Further, harder and stronger materials are less forgiving when contacting plant roots and may result in greater root damage.

A further problem encountered when using these prior devices is the loss of the soil samples, or portions thereof, from the pockets when the tool is withdrawn from the soil. In addition, soil from different depths may be intermixed with the original soil sample as the tool is withdrawn. The intermixed soil samples could result in inaccurate soil information and, ultimately, result in poor plant growth.

Accordingly, there is a need in the art for an improved hand held soil sampling probe which is easy to use, has multiple slots for obtaining soil samples, has substrated structural rigidity, retains the integrity of the soil samples as the probe is withdrawn from the soil and is relatively inexpensive to manufacturer.

SUMMARY OF THE INVENTION

This need is met by the soil sampling probe of the present invention comprising a handle for grasping the probe and a rod member defining a number of soil sampling slots for collecting and retaining soil samples. The soil sampling slots slope inwardly and downwardly into the rod member. A rib is formed adjacent the slots to reinforce and rigidify the rod member in the area of the slots. The rib is preferably tapered on each end to facilitate entering and exiting the soil.

In accordance with one aspect of the present invention, a soil sampling probe comprises a handle for grasping the probe and a rod member. The rod member may have a substantially circular cross sectional shape and defines at least one soil sampling slot positioned serially along a slot portion of the rod member. The rod member includes a handle end connected to the handle and a soil penetrating end opposite the handle end for penetrating into soil. Each of the at least one soil sampling slot slopes inwardly and downwardly toward the soil penetrating end into the rod member to form an extended substantially vertical lip for cutting and retaining soil within the slots. The extended lip may be tapered to further facilitate cutting the soil.

To sample the soil, the probe is inserted into the soil until one or more of the slots are beneath the soil surface. The probe is then rotated generally about a longitudinal axis of the rod member to substantially fill at least one of the at least one soil sampling slot with soil. After one or more slots are filled, the probe is withdrawn from the soil to provide at least one soil sample.

The handle preferably comprises an annular hook which is integrally connected to the rod member for grasping the probe when in use and hanging the probe when not in use. For ease of manufacture and to lessen the weight of the probe, the rod member is preferably made of non-toxic plastic. To reinforce and rigidify the rod member, a rib is formed along the slot portion of the rod member. The rib is preferably tapered at each end to facilitate insertion of the probe into the soil and removal of the probe from the soil.

The soil penetrating end of the rod member may have any shape which can be relatively easily inserted into the soil. It is preferred that the soil penetrating end have a conical shape, however, other shapes, such as a wedge shape, may also be suitable.

In accordance with another aspect of the present invention, a soil sampling probe comprises a rod member defining at least one soil sampling slot positioned serially along a slot portion of the rod member. Each of the slots slope inwardly and downwardly into the rod member. The rod member includes a handle end for grasping the rod member, a soil penetrating end opposite the handle end for penetrating into soil, and at least one rib for reinforcing and rigidifying at least the slot portion of the rod member. Preferably, the handle is an annular hook integrally connected to the rod member.

It is, thus, a feature of the present invention to provide an improved soil sampling probe which has multiple slots sloped inwardly and downwardly in the probe for obtaining soil samples, which has substantial structural rigidity, which retains the integrity of the soil samples as the probe is withdrawn from the soil, and which is relatively inexpensive to manufacture.

These and other features and advantages of the present invention will become apparent from the following detailed description, the accompanying drawings and the appended claims.

BRIEF DESCRIPTION OF THE DRAWINGS

FIG. 3 is a side view of the soil sampling probe; and

FIG. 4 is a front view of the soil sampling probe

DETAILED DESCRIPTION OF THE INVENTION

Figure 1:
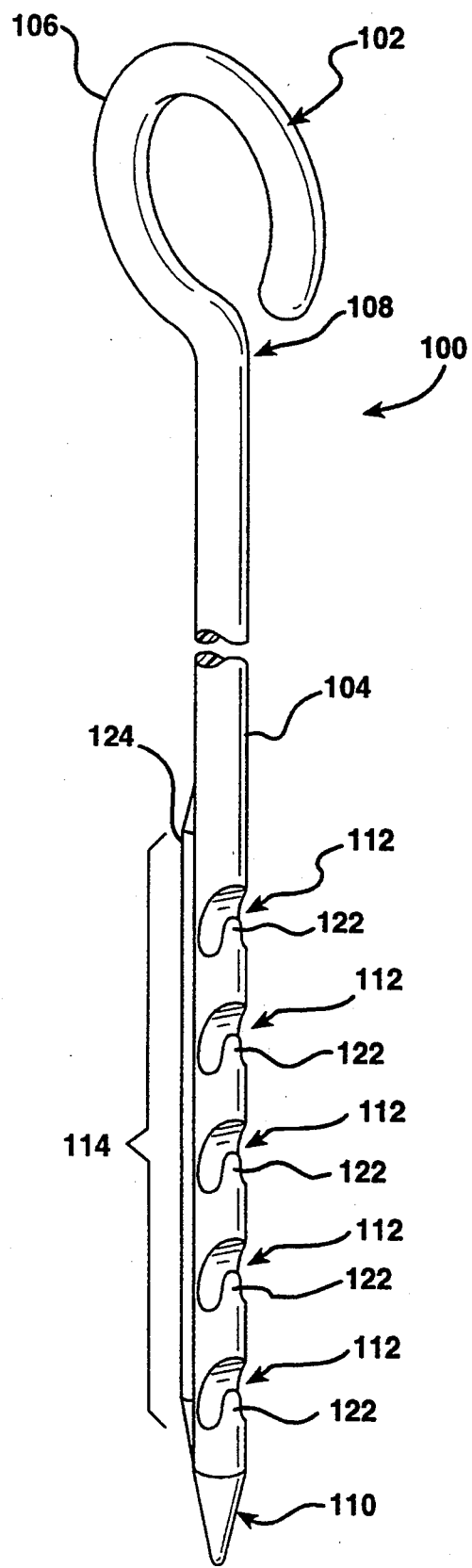
FIG. 1 is a perspective, broken view of a soil sampling probe including a conically-shaped soil penetrating end in accordance with the present invention.

A soil sampling probe 100 having a handle 102 and a rod member 104 having a substantially circular cross sectional shape in accordance with the present invention is shown in FIG. 1. The handle 102 may consist of a annular hook 106 for grasping the probe 100. The annular hook 106 also provides a convenient means to removably mount the probe 100 onto a belt loop, pants pocket or a peg board for transport or storage. The annular hook 106 is connected to a handle end 108 of the rod member 104.

To reduce the weight and manufacturing costs of the probe 100, the rod member 104 may be made of a non-toxic plastic. The handle 102 and the rod member 104 is preferably fabricated as a single integral unit to further reduce the weight and manufacturing costs of the probe 100.

Figure 1A:
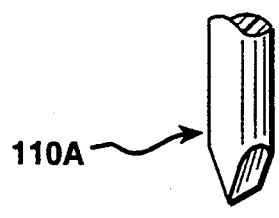
FIG. 1A is a perspective view of an alternative soil penetrating end for the soil sampling probe shown in FIG. 1 having a wedge-shape.

A soil penetrating end 110 positioned opposite the handle end 108 of the rod member 104 is contoured to permit relatively easy insertion of the probe 100 into the soil to be tested. As shown in FIG. 1, the soil penetrating end 110 preferably has a conical shape, however, other shapes may be advantageously employed, for example a wedge shape 110A as shown in FIG. 1A. The rod member 104 defines at least one soil sampling slot 112 positioned serially along a slot portion 114 of the member 104. Although the rod member 104 is illustrated as having five slots 112 in the drawings, it should be understood that any reasonable number of slots may be advantageously employed in the present invention.

Figure 2:
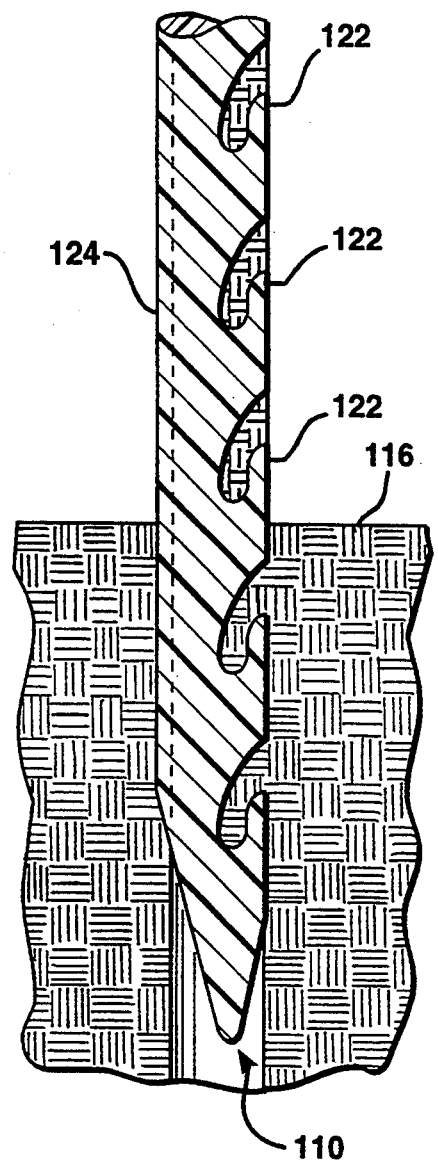
FIG. 2 is a partial cross sectional view of the soil sampling probe being withdrawn from the soil taken along section lines 2—2 in FIG. 3.

The procedure for testing soil 116 for moisture and soil consistency with the probe 100 will now be described with reference to FIGS. 2 through 4. The soil penetrating end 110 is forced, as shown by arrow 118, into the soil 116 until the five slots 112 are inserted into the soil 116. The five soil sampling slots 112 extend into the soil 116 to five different depths. As should be apparent, not all of the slots 112 need to be inserted into the soil 116, however, soil test samples will only be obtained for the slots 112 inserted into the soil 116.

After inserting the probe 100 into the soil 116, the probe 100 is rotated substantially about a longitudinal axis A of the rod member 104, as shown by arrow 120. As the slots 112 are rotated in the soil 116, each of the slots 112 are substantially filled with soil samples from their respective depths. The probe 100 is then removed from the soil 116 with the slots 112 substantially filled with the soil samples. Thereafter, soil from the five depths can be analyzed for the moisture content and the consistency of the soil.

The soil sampling slots 112 of the present invention are uniquely designed to collect and retain samples of soil as the probe 100 is withdrawn from the soil. The slots 112 slope inwardly and downwardly toward the soil penetrating end 110 of the rod member 104. By thus defining the slots 112, extended, substantially vertical lips 122 are formed in the rod member 104 which are ideally suited to cut the soil and assist in retaining soil samples in the respective slots 112. To further assist in cutting the soil, the vertical lips 122 are tapered to form a substantially sharp cutting edge.

As is readily apparent, the slot portion 114 is the structurally weakest area of the rod member 104. To reinforce and rigidify this area, a rib 124 is formed generally in the slot portion 114 of the rod member 104. The rib 124 is gradually tapered on each end to facilitate insertion and withdraw of the rod member 104 from the soil 116. The reinforcement of the rib 124 permits the rod member 104 to be smaller in diameter than other non-ribbed probes while still maintaining its structural integrity during insertion and removal from the soil.

Having thus described the invention in detail by way of reference to preferred embodiments thereof, it will be apparent that other modifications and variations are possible without departing from the scope of tile invention defined in the appended claims.

What is claimed is:

1. A soil sampling probe comprising:
   a handle for grasping said probe; and
   a rod member defining a plurality of soil sampling slots positioned serially along a slot portion of said rod member and including a handle end connected to said handle and a soil penetrating end opposite said handle end for penetrating into soil, each of said plurality of soil sampling slots sloping inwardly and downwardly toward said soil penetrating end into said rod member to form an extended substantially vertical lip for cutting and retaining soil within each of said plurality of soil sampling slots,
   wherein said probe is inserted into soil, rotated substantially about a longitudinal axis of said rod member to substantially fill at least one of said plurality of soil sampling slots with soil and withdrawn to provide at least one soil sample.

2. The soil sampling probe as recited in claim 1 wherein said handle comprises an annular hook for grasping said probe.

3. The soil sampling probe as recited in claim 2 wherein said annular hook is integrally connected to said handle end of said rod member.

4. The soil sampling probe as recited claim 1 wherein said rod member has a substantially circular cross sectional shape.

5. The soil sampling probe as recited in claim 1 wherein said soil penetrating end has a conical shape.

6. The soil sampling probe as recited in claim 1 wherein said soil penetrating end has a wedge shape.

7. The soil sampling probe as recited in claim 1 wherein said rod member is plastic.

8. The soil sampling probe as recited in claim 1 wherein said extended lip is tapered to facilitate cutting soil.

9. A soil sampling probe comprising:
   a handle for grasping said probe; and a rod member defining a plurality of soil sampling slots positioned serially along a slot portion of said rod member and including a handle end connected to said handle and a soil penetrating end opposite said handle end for penetrating into soil, each of said plurality of soil sampling slots sloping inwardly and downwardly toward said soil penetrating end into said rod member to form an extended substantially vertical lip for cutting and retaining soil within each of said plurality of soil sampling slot, said rod member further comprising a rib for reinforcing and rigidifying at least said slot portion of said rod member, wherein said probe is inserted into soil, rotated substantially about a longitudinal axis of said rod member to substantially fill at least one of said plurality of soil sampling slots with soil and withdrawn to provide at least one soil sample.

10. The soil sampling probe as recited in claim 5 wherein said rib is tapered at each end to facilitate insertion into the soil and removal from the soil.

11. A soil sampling probe comprising a rod member defining a plurality of soil sampling slots positioned serially along a slot portion of said rod member, each of said plurality of soil sampling slots sloping inwardly and downwardly into said rod member, and including a handle end for grasping said rod member, a soil penetrating end shaped and located opposite said handle end for penetrating into soil, and at least one rib for reinforcing and rigidifying at least said slot portion of said rod member, wherein said probe is inserted into the soil, rotated substantially about a longitudinal axis of said rod member to substantially fill at least one of said plurality of soil sampling slots with soil and withdrawn to provide at least one soil sample.

12. The soil sampling probe as recited in claim 11 wherein said handle end comprises an annular hook integrally connected to said rod member.

13. The soil sampling probe as recited in claim 12 wherein said rod mender has a substantially circular cross sectional shape.

14. The soil sampling probe as recited in claim 11 wherein said at least one rib has at least one tapered end.

15. The soil sampling probe as recited in claim 11 wherein said rod member is plastic.

* * * * *

UNITED STATES PATENT AND TRADEMARK OFFICE
CERTIFICATE OF CORRECTION

PATENT NO. : 5,411,103
DATED : May 2, 1995
INVENTOR(S) : Mary K. Werner

It is certified that error appears in the above-indentified patent and that said Letters Patent is hereby corrected as shown below:

Col. 5, line 19,     "claim 5" should read --claim 9--.

Signed and Sealed this

Thirty-first Day of October 1995

Attest:

BRUCE LEHMAN

*Attesting Officer*     *Commissioner of Patents and Trademarks*